(12) United States Patent
Richter

(10) Patent No.: US 11,726,551 B1
(45) Date of Patent: Aug. 15, 2023

(54) PRESENTING CONTENT BASED ON ACTIVITY

(71) Applicant: Apple Inc., Cupertino, CA (US)

(72) Inventor: Ian M. Richter, Los Angeles, CA (US)

(73) Assignee: APPLE INC., Cupertino, CA (US)

(*) Notice: Subject to any disclaimer, the term of this patent is extended or adjusted under 35 U.S.C. 154(b) by 0 days.

(21) Appl. No.: 17/381,957

(22) Filed: Jul. 21, 2021

Related U.S. Application Data

(60) Provisional application No. 63/070,608, filed on Aug. 26, 2020.

(51) Int. Cl.
*G06F 3/01* (2006.01)
*A61B 5/11* (2006.01)
*A63F 13/428* (2014.01)

(52) U.S. Cl.
CPC ............ *G06F 3/011* (2013.01); *A61B 5/1122* (2013.01); *A61B 5/1123* (2013.01); *A63F 13/428* (2014.09); *A61B 5/11* (2013.01); *A61B 5/1114* (2013.01); *A61B 5/1126* (2013.01)

(58) Field of Classification Search
CPC .... G06F 3/011; G06F 3/04815; A61B 5/1114; A61B 5/1122; A61B 5/1126; A61B 5/744; A61B 5/0205; A61B 5/7267; A61B 2562/0219; A63F 13/428; G01B 21/00; G06T 7/251; G06T 13/40; G06T 19/003
See application file for complete search history.

(56) References Cited

U.S. PATENT DOCUMENTS

| | | |
|---|---|---|
| 10,319,352 B2 | 6/2019 | Kar et al. |
| 2011/0021273 A1 | 1/2011 | Buckley et al. |
| 2013/0194066 A1* | 8/2013 | Rahman .......... G05B 1/01 340/5.51 |
| 2018/0350144 A1* | 12/2018 | Rathod .......... G06T 13/40 |

FOREIGN PATENT DOCUMENTS

CN    109348400 A    2/2019

* cited by examiner

*Primary Examiner* — Adam R. Giesy
(74) *Attorney, Agent, or Firm* — Fernando & Partners, LLP

(57) ABSTRACT

Various implementations disclosed herein include devices, systems, and methods for presenting content based on activity. In various implementations, a device includes a sensor, a non-transitory memory and one or more processors coupled with the sensor and the non-transitory memory. In various implementations, a method includes obtaining environmental data via the sensor. In some implementations, the method includes identifying a physical activity of a user of the device based on the environmental data. In some implementations, the method includes obtaining contextual data associated with the device or the user of the device. In some implementations, the method includes presenting content based on the physical activity of the user and the contextual data associated with the device or the user of the device.

23 Claims, 9 Drawing Sheets

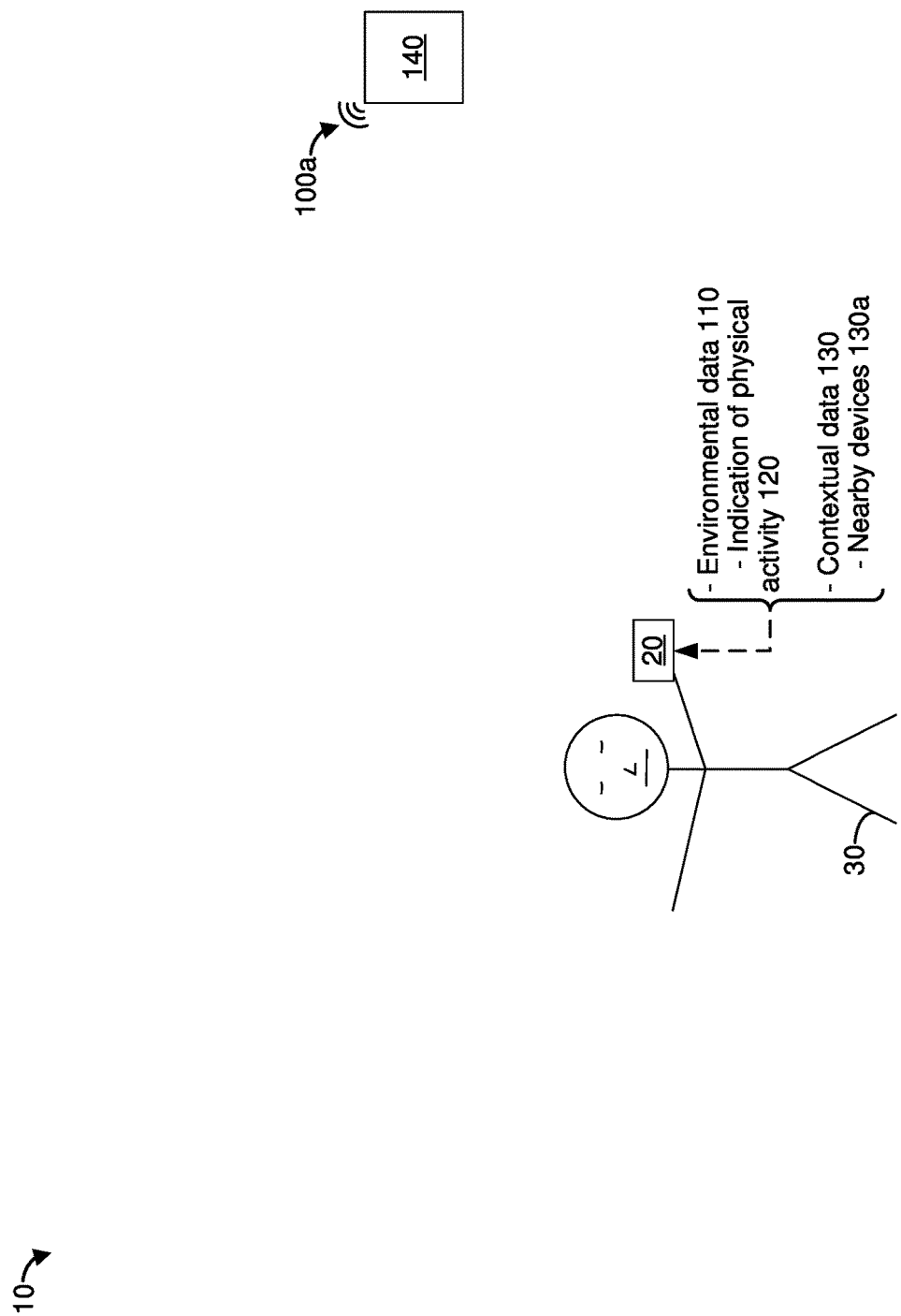

PRESENTING CONTENT BASED ON ACTIVITY

CROSS-REFERENCE TO RELATED APPLICATION

This application claims the benefit of U.S. Provisional Patent App. No. 63/070,608, filed on Aug. 26, 2020, which is incorporated by reference in its entirety.

TECHNICAL FIELD

The present disclosure generally relates to presenting content based on activity.

BACKGROUND

Some devices are capable of generating and presenting extended reality (XR) environments. Some XR environments include virtual environments that are simulated replacements of physical environments. Some XR environments include augmented environments that are modified versions of physical environments. Some devices that present XR environments include mobile communication devices such as smartphones, tablets, head-mountable displays (HMDs), eyeglasses, heads-up displays (HUDs), and optical projection systems.

BRIEF DESCRIPTION OF THE DRAWINGS

So that the present disclosure can be understood by those of ordinary skill in the art, a more detailed description may be had by reference to aspects of some illustrative implementations, some of which are shown in the accompanying drawings.

FIGS. 1A-1F are diagrams of an example operating environment in accordance with some implementations.

Figure 1A:
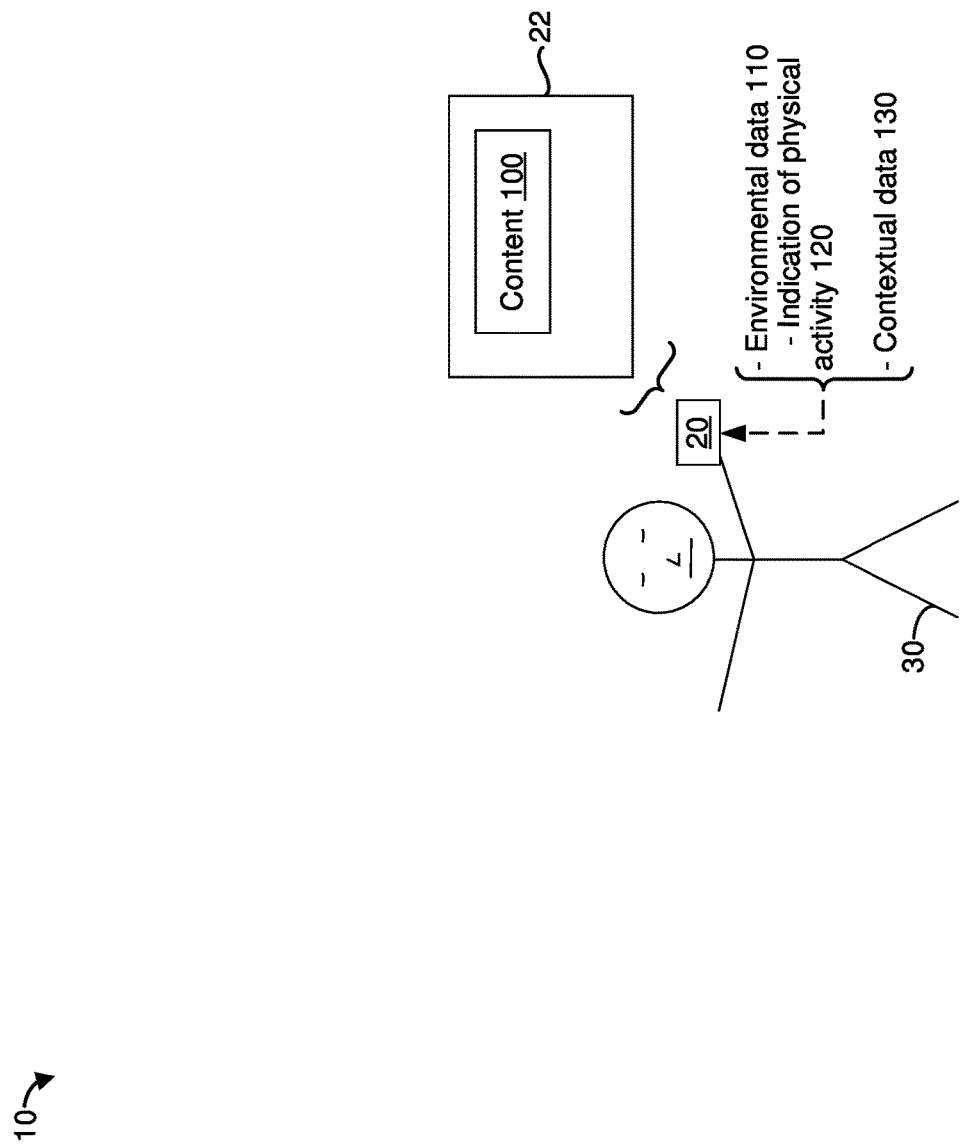

In accordance with common practice the various features illustrated in the drawings may not be drawn to scale. Accordingly, the dimensions of the various features may be arbitrarily expanded or reduced for clarity. In addition, some of the drawings may not depict all of the components of a given system, method or device. Finally, like reference numerals may be used to denote like features throughout the specification and figures.

SUMMARY

Various implementations disclosed herein include devices, systems, and methods for presenting content based on activity. In various implementations, a device includes a sensor, a non-transitory memory and one or more processors coupled with the sensor and the non-transitory memory. In various implementations, a method includes obtaining environmental data via the sensor. In some implementations, the method includes identifying a physical activity of a user of the device based on the environmental data. In some implementations, the method includes obtaining contextual data associated with the device or the user of the device. In some implementations, the method includes presenting content based on the physical activity of the user and the contextual data associated with the device or the user of the device.

In accordance with some implementations, a device includes one or more processors, a non-transitory memory, and one or more programs. In some implementations, the one or more programs are stored in the non-transitory memory and are executed by the one or more processors. In some implementations, the one or more programs include instructions for performing or causing performance of any of the methods described herein. In accordance with some implementations, a non-transitory computer readable storage medium has stored therein instructions that, when executed by one or more processors of a device, cause the device to perform or cause performance of any of the methods described herein. In accordance with some implementations, a device includes one or more processors, a non-transitory memory, and means for performing or causing performance of any of the methods described herein.

DESCRIPTION

Numerous details are described in order to provide a thorough understanding of the example implementations shown in the drawings. However, the drawings merely show some example aspects of the present disclosure and are therefore not to be considered limiting. Those of ordinary skill in the art will appreciate that other effective aspects and/or variants do not include all of the specific details described herein. Moreover, well-known systems, methods, components, devices, and circuits have not been described in exhaustive detail so as not to obscure more pertinent aspects of the example implementations described herein.

A physical environment refers to a physical world that people can sense and/or interact with without aid of electronic devices. The physical environment may include physical features such as a physical surface or a physical object. For example, the physical environment corresponds to a physical park that includes physical trees, physical buildings, and physical people. People can directly sense and/or interact with the physical environment such as through sight, touch, hearing, taste, and smell. In contrast, an extended reality (XR) environment refers to a wholly or partially simulated environment that people sense and/or interact with via an electronic device. For example, the XR environment may include augmented reality (AR) content, mixed reality (MR) content, virtual reality (VR) content, and/or the like. With an XR system, a subset of a person's physical motions, or representations thereof, are tracked, and, in response, one or more characteristics of one or more virtual objects simulated in the XR environment are adjusted in a manner that comports with at least one law of physics. As one example, the XR system may detect head movement and, in response, adjust graphical content and an acoustic field presented to the person in a manner similar to how such views and sounds would change in a physical environment. As another example, the XR system may detect movement of the electronic device presenting the XR environment (e.g., a mobile phone, a tablet, a laptop, or the like) and, in response, adjust graphical content and an acoustic field presented to the person in a manner similar to how such views and sounds would change in a physical environment. In some situations (e.g., for accessibility reasons), the XR system may adjust characteristic(s) of graphical content in the XR environment in response to representations of physical motions (e.g., vocal commands).

There are many different types of electronic systems that enable a person to sense and/or interact with various XR environments. Examples include head mountable systems, projection-based systems, heads-up displays (HUDs), vehicle windshields having integrated display capability, windows having integrated display capability, displays formed as lenses designed to be placed on a person's eyes (e.g., similar to contact lenses), headphones/earphones, speaker arrays, input systems (e.g., wearable or handheld controllers with or without haptic feedback), smartphones, tablets, and desktop/laptop computers. A head mountable system may have one or more speaker(s) and an integrated opaque display. Alternatively, a head mountable system may be configured to accept an external opaque display (e.g., a smartphone). The head mountable system may incorporate one or more imaging sensors to capture images or video of the physical environment, and/or one or more microphones to capture audio of the physical environment. Rather than an opaque display, a head mountable system may have a transparent or translucent display. The transparent or translucent display may have a medium through which light representative of images is directed to a person's eyes. The display may utilize digital light projection, OLEDs, LEDs, uLEDs, liquid crystal on silicon, laser scanning light source, or any combination of these technologies. The medium may be an optical waveguide, a hologram medium, an optical combiner, an optical reflector, or any combination thereof. In some implementations, the transparent or translucent display may be configured to become opaque selectively. Projection-based systems may employ retinal projection technology that projects graphical images onto a person's retina. Projection systems also may be configured to project virtual objects into the physical environment, for example, as a hologram or on a physical surface.

Certain actions of a user in a physical environment (e.g., in the real-world) appear less realistic or less enjoyable without accompanying content (e.g., without a sound, a video or an XR object). For example, if two people are using broomsticks to imitate a sword fight, their actions may not sound like a sword fight without the metallic clashing sound that swords generate when they collide with each other. Similarly, if a user starts performing a dance move (e.g., a twirl), the dance move may not appear as realistic without some accompanying music. In another example, if two kids are playing a game where they act like dragons, the game may appear more realistic if they could throw virtual dragon fire at each other.

Given the vast amount of available content, it is sometimes difficult for a user to search for suitable content. Moreover, timing the playback of an existing content item so that the playing of the content item coincides with an appropriate action is difficult. Additionally, if the user selects a particular content item (e.g., a particular music item), then the user may be restricted to performing an action that is appropriate for the content item (e.g., the user may be restricted to dancing at a speed that matches a tempo of a selected music item). As such, selecting an existing content item often limits the user's ability to perform certain actions in the physical environment.

The present disclosure provides methods, systems, and/or devices for presenting content based on a physical activity of a user and contextual data associated with the user or a device of the user. A device detects a physical activity that the user is performing, and presents content based on the physical activity and contextual data. For example, the device detects that the user is initiating a twirl, and the device plays music that is appropriate for a twirl. In another example, the device detects that the user is pretending to be in a sword fight, and the device plays a metallic clashing sound when an object that the user is holding (e.g., a broomstick) collides with another object (e.g., another broomstick). Presenting content based on the physical activity of the user enhances a user experience of the device by allowing the user to immerse into the physical activity.

The device can detect the physical activity of the user via a depth sensor, an image sensor or an audio sensor. The device can select a presentation mode (e.g., a modality) for presenting the content based on the physical activity or the contextual data. The device can present different content based on a location of the device. For example, the device can play different sound effects in private settings and public settings. The device can present different content based on a current time. For example, the device can play different music during the day and night.

The device can present content based on a function of other people that are around the user. For example, if the user is with his/her spouse, the device can play romantic music. In another example, if the user is with his/her child(ren), the device can play child-friendly music. Presenting content based on a relationship of the user with a nearby person tends to result in the presentation of content that is more appropriate or more relevant to the user and the nearby person.

The device can generate the content by mixing (e.g., combining) existing content items. For example, the device can generate music that is a fusion of songs from different genres. The device can adapt the content based on the physical activity. For example, as the device detects changes in a body pose of the user, the device can modify the music being played in order to match the changes in the body pose.

Presenting the content based on the physical activity and the contextual data reduces the need for user inputs that correspond to the user manually searching for appropriate content and playing the content. Reducing unnecessary user inputs tends to increase operability of a battery-powered device by prolonging a battery of the battery-powered device. Presenting the content based on the physical activity and the contextual data tends to make the physical activity appear more realistic thereby enhancing a user experience of the device.

FIG. 1A is a diagram of an example operating environment 10 in accordance with some implementations. While pertinent features are shown, those of ordinary skill in the art will appreciate from the present disclosure that various other features have not been illustrated for the sake of brevity and so as not to obscure more pertinent aspects of the example implementations disclosed herein. To that end, as a non-limiting example, the operating environment 10 includes an electronic device 20.

In some implementations, the electronic device 20 includes a handheld computing device that can be held by a user 30. For example, in some implementations, the electronic device 20 includes a smartphone, a tablet, a media player, a laptop, or the like. In some implementations, the electronic device 20 includes a wearable computing device that can be worn by the user 30. For example, in some implementations, the electronic device 20 includes a head-mountable device (HMD) that can be worn around a head of the user 30, an electronic watch or a pair of headphones.

In some implementations, the electronic device 20 includes an optical see-through display. For example, the electronic device 20 includes an HMD with an optical see-through display. In various implementations, the optical see-through display is transparent. In some implementations, the optical see-through display includes an additive light field display ("additive display", hereinafter for the sake of brevity). In some implementations, the additive display includes a set of one or more optical holographic optical elements (HOEs). In some implementations, the additive display displays content by adding light and does not subtract or remove light.

In various implementations, the electronic device 20 obtains environmental data 110 that includes an indication 120 of a physical activity that the user 30 is performing. In some implementations, the electronic device 20 obtains contextual data 130 that indicates a context of the electronic device 20 or the user 30. In various implementations, the electronic device 20 presents content 100 based on the indication 120 of the physical activity and the contextual data 130. In some implementations, the electronic device 20 displays a visual representation of the content 100 on a display 22 of the electronic device 20.

In some implementations, the environmental data 110 includes depth data that is captured from a depth sensor. In such implementations, the electronic device 20 identifies the physical activity that the user 30 is engaged in based on the depth data. In some implementations, the environmental data 110 includes image data that is captured from an image sensor (e.g., a camera). In such implementations, the electronic device 20 identifies the physical activity in which the user 30 is engaged based on the image data. For example, in some implementations, the electronic device 20 determines a body pose of the user 30 and compares the body pose of the user 30 with body poses associated with known activities. If the body pose of the user 30 matches a body pose associated with a particular activity, the electronic device 20 determines that the user 30 is performing that particular activity.

In some implementations, the environmental data 110 includes audible signal data that is captured via an audio sensor (e.g., a microphone). In such implementations, the electronic device 20 identifies the physical activity that the user 30 is performing based on the audible signal data. For example, if a sound represented by the audible signal data matches a sound associated with a particular physical activity, the electronic device 20 determines that the user 30 is engaged in that particular physical activity.

In various implementations, the contextual data 130 includes a location of the electronic device 20, a current time, a dietary intake of the user 30, and/or an energy level of the user 30. In some implementations, the contextual data 130 indicates a relationship of the user 30 with another person that is in the operating environment 10. In some implementations, the contextual data 130 indicates types of other devices that are near the electronic device 20. In some implementations, the contextual data 130 indicates a content preference of the user 30 (e.g., based on historical content consumption of the user 30 or a user-specified content preference).

In various implementations, there are multiple content items that correspond to the physical activity of the user 30. In such implementations, the electronic device 20 selects the content 100 such that the content 100 is suitable based on the contextual data 130. In some implementations, the electronic device 20 utilizes the contextual data 130 to filter out content items that are inappropriate or irrelevant based on a context of the user 30 and/or the electronic device 20 indicated by the contextual data 130. For example, in some implementations, the electronic device 20 selects the content 100 based on the location of the electronic device 20. In some implementations, the electronic device 20 selects the content 100 based on a type of location of the electronic device 20. For example, if the location of the electronic device 20 is a public location (e.g., a location where other people can see or listen to the content 100 as the content 100 is being presented on the electronic device 20, for example, a restaurant, a coffee shop, a store, etc.), the electronic device 20 selects the content 100 such that the content 100 is suitable for public locations. If the location of the electronic device 20 is a private location (e.g., a location where other people cannot see or listen to the content 100 as the content 100 is being presented on the electronic device 20, for example, a home), the electronic device 20 selects the content 100 such that the content 100 is suitable for private locations.

Figure 1B:
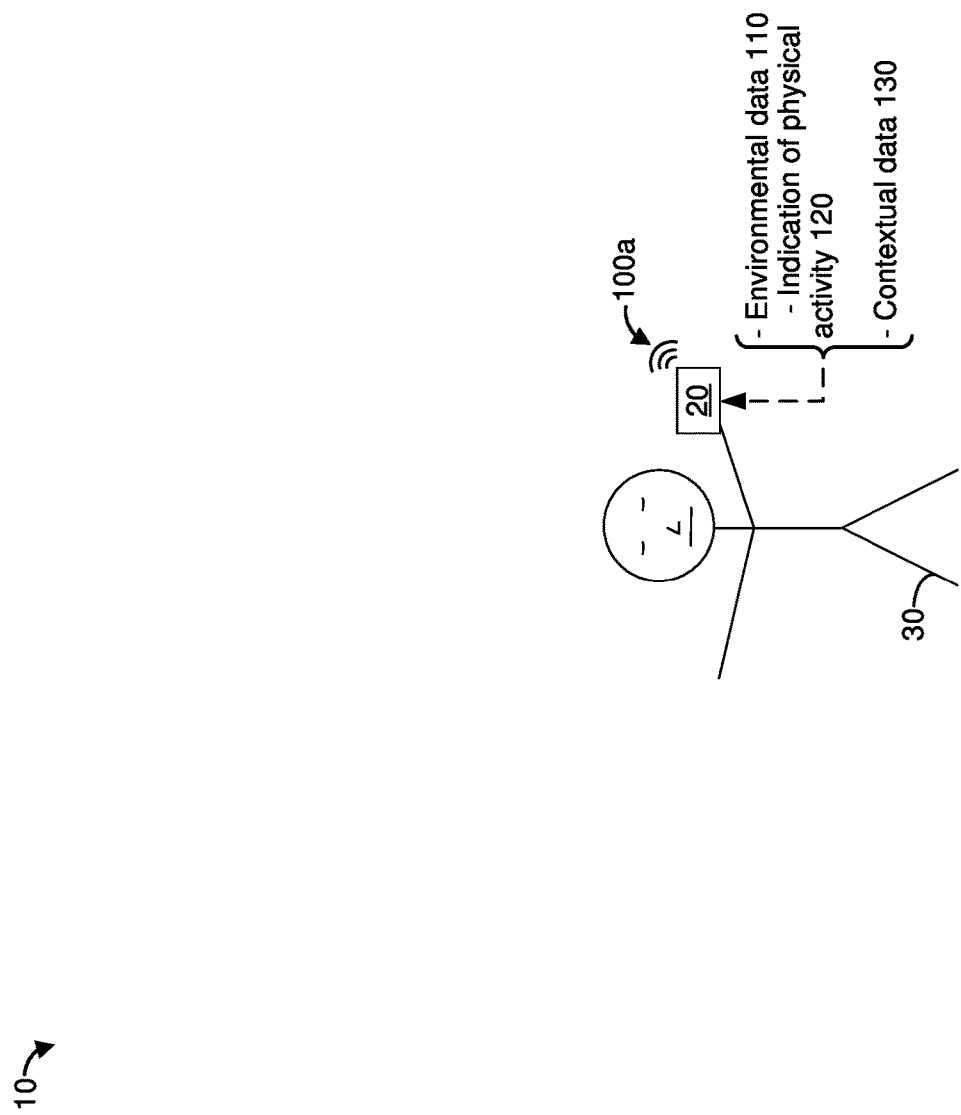

Referring to FIG. 1B, in some implementations, the electronic device 20 selects a presentation mode (e.g., a modality) of the content based on the indication 120 of the physical activity and the contextual data 130. For example, as shown in FIG. 1B, in some implementations, the electronic device 20 plays audio 100a corresponding to the content 100 shown in FIG. 1A. More generally, in various implementations, the electronic device 20 selects an audio presentation mode for the content based on the physical activity or the contextual data 130. For example, in some implementations, the electronic device 20 selects the audio presentation mode when the electronic device 20 determines that the user 30 may not be able to view visual content, for example, because the physical activity prevents the user 30 from looking at the display 22. In some implementations, the electronic device 20 selects the audio presentation mode when the contextual data 130 indicates that the user 30 may not be able to view the display 22. For example, in some implementations, the electronic device 20 selects the audio presentation mode when the contextual data 130 indicates that the electronic device 20 is located in a public location and the content 100 is not suitable to be viewed in a public location (e.g., because the content 100 is private or confidential).

In some implementations, the environmental data 110 includes accelerometer data that indicates that the user 30 is walking or running. For example, in some implementations, the electronic device 20 includes a wearable computing device such as an electronic watch that detects that the user 30 is walking. In some implementations, the electronic device 20 provides the user 30 an option to play a sound that coincides with each footstep that the user 30 takes in order to provide an appearance that the user 30 is walking in a different environment. For example, in some implementations, the electronic device 20 provides the user 30 an option to play a sound that corresponds to footsteps being taken on a sandy beach in order to provide an appearance that the user 30 is walking on a beach even though the user 30 may be walking on a concrete sidewalk. As another example, in some implementations, the electronic device 20 provides the user 30 an option to play a sound that corresponds to footsteps being taken on fallen leaves in a forest in order to provide an appearance that the user 30 is walking in a forest even though the user 30 may be walking on a concrete sidewalk.

Referring to FIG. 1C, in some implementations, the contextual data 130 indicates types of nearby devices 130a. For example, in some implementations, the contextual data 130 indicates that an external speaker 140 ("speaker 140", hereinafter for the sake of brevity) is within a threshold distance of the electronic device 20. In the example of FIG. 1C, the electronic device 20 plays the audio 100a corresponding to the content 100 on the speaker 140. In some implementations, a sound quality of the speaker 140 is better than a sound quality of a speaker integrated into the electronic device 20. In some implementations, the speaker 140 is a wireless speaker, and the electronic device 20 wirelessly transmits audible signal data to the speaker 140. As such, in some implementations, playing the audio 100a on the speaker 140 results in an improved user experience than playing the audio 100a on the electronic device 20. In some implementations, the types of nearby devices 130a includes an external display screen (e.g., a television), and the electronic device 20 plays the content 100 on the external display screen (e.g., instead of or in addition to playing the content 100 on the electronic device 20). In some implementations, if there are multiple content items that correspond to the physical activity that the user 30 is performing, the electronic device 20 selects a subset of the content items based on the nearby devices 130a.

Figure 1D:
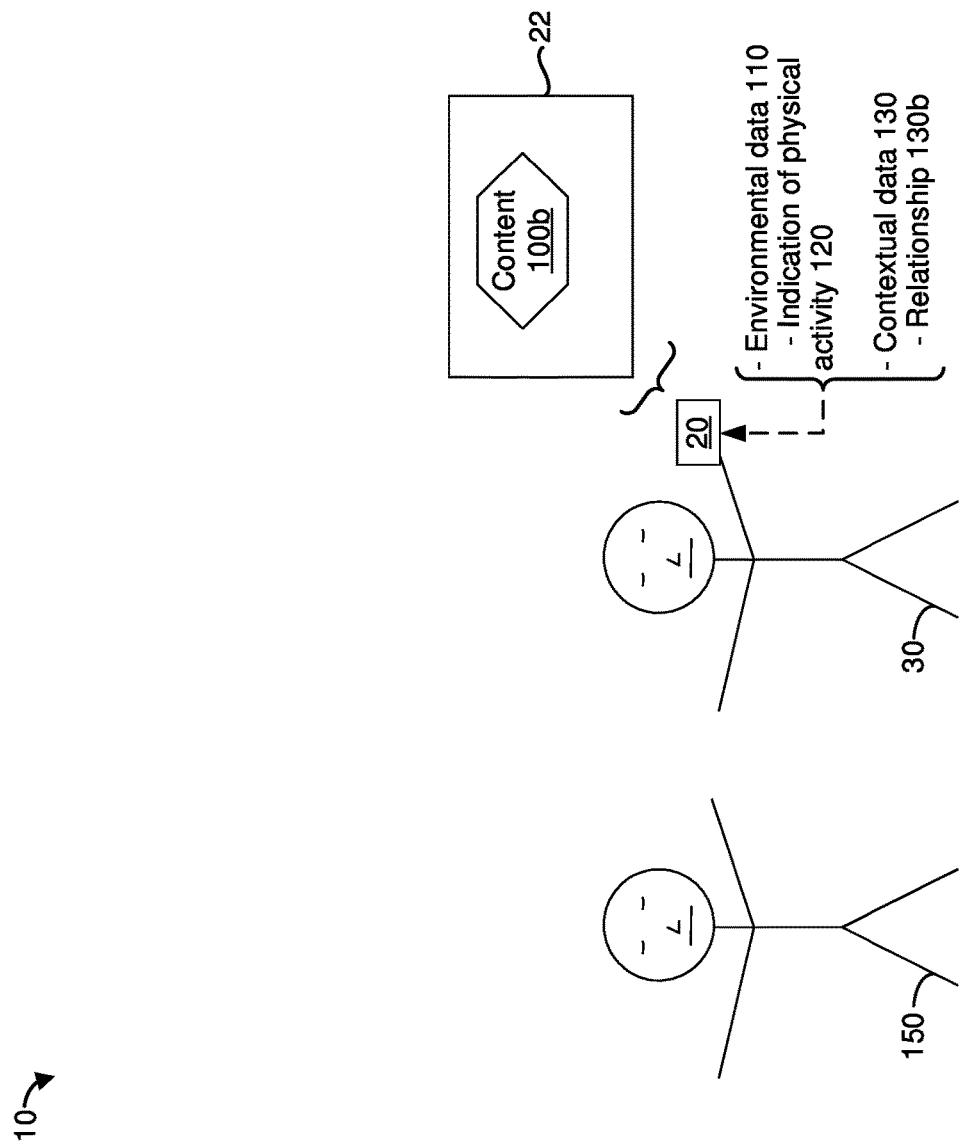

Referring to FIG. 1D, in some implementations, another person 150 is located in the operating environment 10. In some implementations, the contextual data 130 indicates a relationship 130b between the user 30 and the other person 150. For example, in some implementations, the contextual data 130 indicates that the relationship 130b is a familial relationship (e.g., a spousal relationship, a parent-child relationship, etc.), a collegial relationship, or a close friendship. In some implementations, the electronic device 20 presents content 100b based on the relationship 130b between the user 30 and the other person 150. The content 100b is different from the content 100 shown in FIG. 1A. More generally, in various implementations, the electronic device 20 presents different content for different relationships. For example, if the relationship 130b is a spousal relationship and the user 30 is having dinner with his/her spouse, the electronic device 20 plays content suitable for couples (e.g., audio corresponding to a violin being played). As another example, if the relationship 130b is a parent-child relationship and the user 30 is feeding his/her child, the electronic device 20 plays content suitable for children (e.g., video corresponding to children's cartoons). In some implementations, if there are multiple content items that correspond to the physical activity that the user 30 is performing, the electronic device 20 selects a subset of the content items based on the relationship 130b of the user 30 with another person in the physical environment.

Figure 1E:
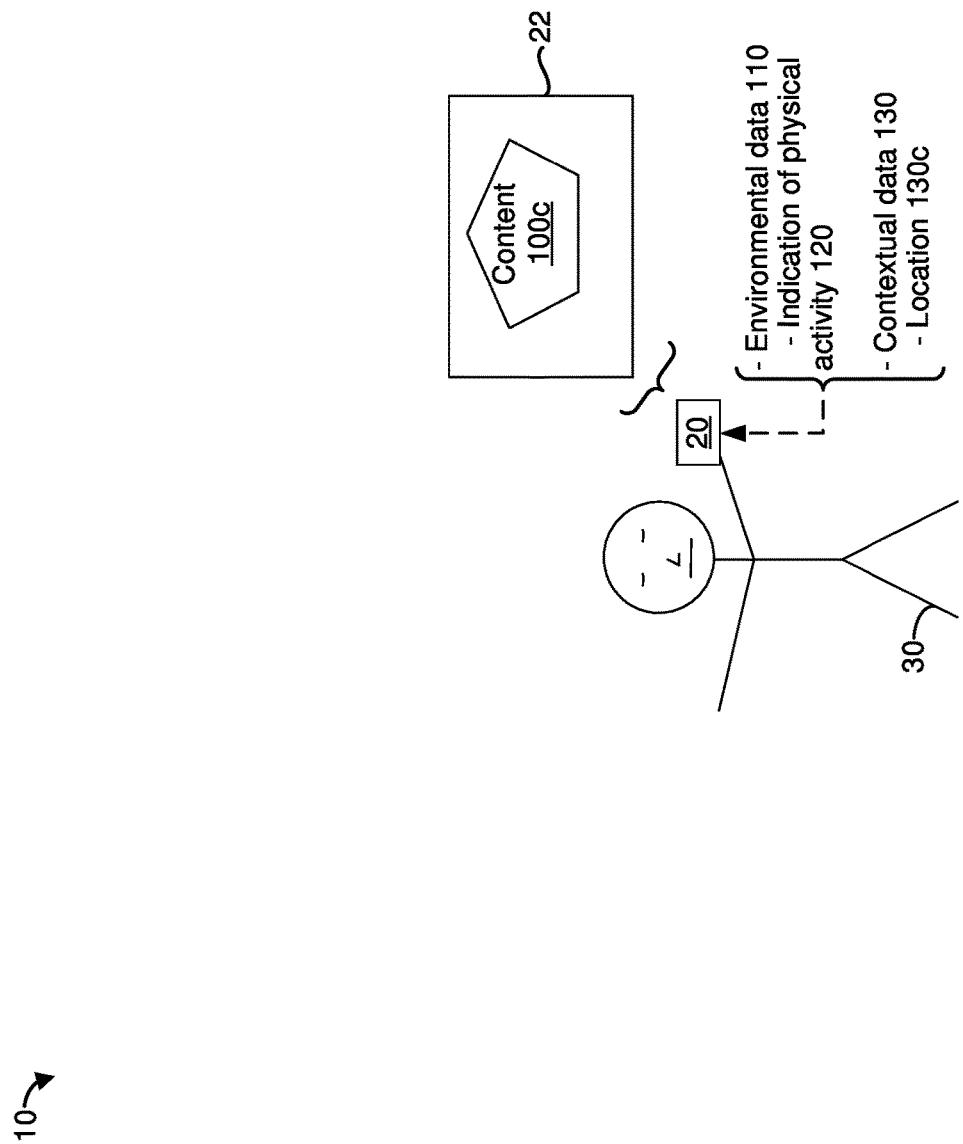

Referring to FIG. 1E, in some implementations, the contextual data 130 indicates a location 130c of the electronic device 20. In some implementations, the location 130c includes a type of location (e.g., a private setting or a public setting). In some implementations, the electronic device 20 presents content 100c based on the location 130c of the electronic device 20. The content 100c is different from the content 100 shown in FIG. 1A and the content 100b shown in FIG. 1D. More generally, in various implementations, the electronic device 20 presents different content for different locations. For example, if the location 130c corresponds to a public setting and the user 30 is dancing, the electronic device 20 plays a public dancing playlist. As another example, if the location 130c corresponds to a private setting and the user 30 is dancing, the electronic device 20 plays a private dancing playlist. In some implementations, if there are multiple content items that correspond to the physical activity that the user 30 is performing, the electronic device 20 selects a subset of the content items based on the location 130c of the electronic device 20.

Figure 1F:
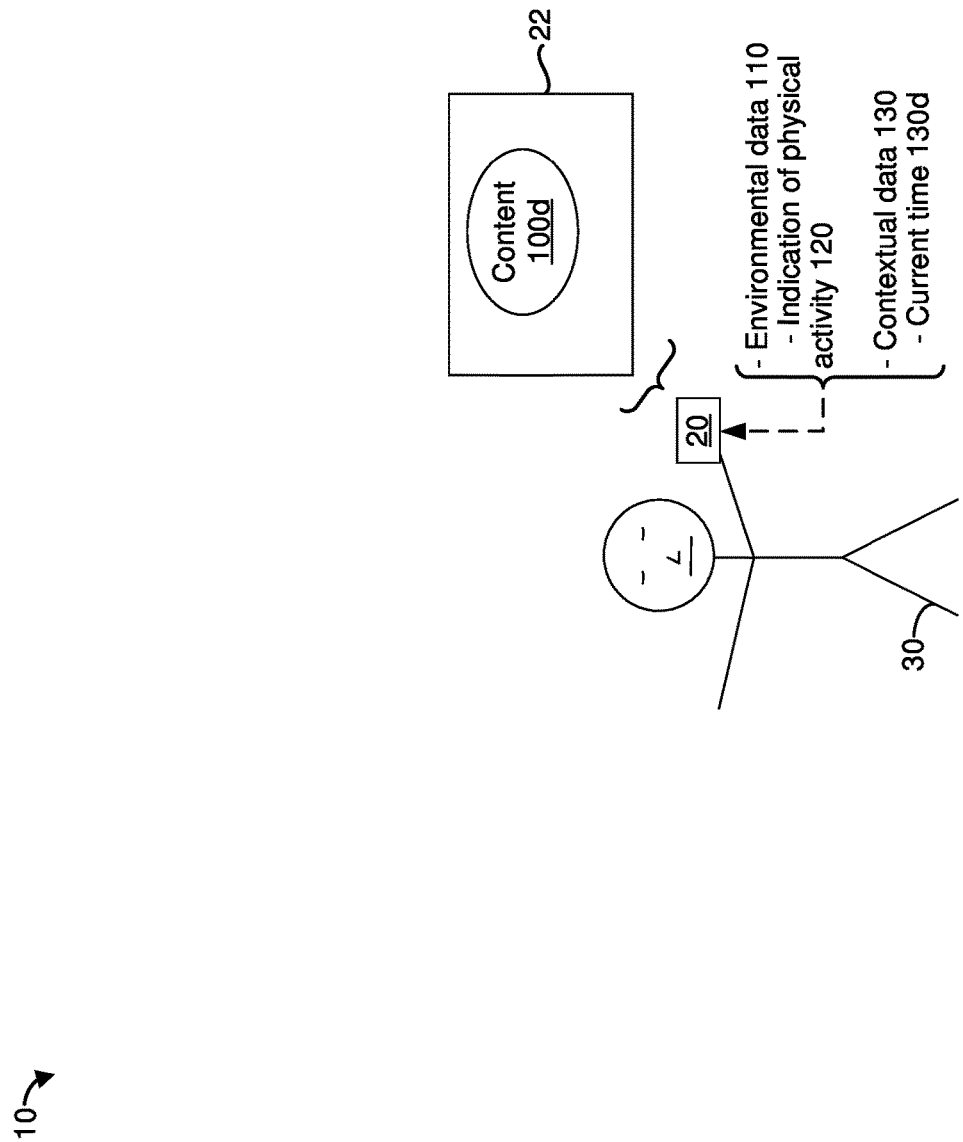

Referring to FIG. 1F, in some implementations, the contextual data 130 indicates a current time 130d. In some implementations, the electronic device 20 presents content 100d based on the current time 130d. The content 100d is different from the content 100 shown in FIG. 1A, the content 100b shown in FIG. 1D and the content 100c shown in FIG. 1E. More generally, in various implementations, the electronic device 20 presents different content for different times. For example, if the user 30 is eating and the current time 130d corresponds to morning, the electronic device 20 plays morning news. As another example, if the user 30 is eating and the current time 130d corresponds to evening, the electronic device 20 plays a sitcom. In some implementations, if there are multiple content items that correspond to the physical activity that the user 30 is performing, the electronic device 20 selects a subset of the content items based on the current time 130d.

In some implementations, the electronic device 20 includes an HMD that is worn by the user 30. In some implementations, the HMD presents (e.g., displays) an XR environment according to various implementations. In such implementations, the electronic device 20 plays the content 100 shown in FIG. 1A, the audio 100a shown in FIGS. 1B and 1C, the content 100b shown in FIG. 1D, the content 100c shown in FIG. 1E, and/or the content 100d shown in FIG. 1F within the XR environment. In some implementations, the HMD includes an integrated display (e.g., a built-in display, for example, a built-in optical see-through display or a built-in opaque display) that displays the XR environment. In some implementations, the HMD includes a head-mountable enclosure. In various implementations, the head-mountable enclosure includes an attachment region to which another device with a display can be attached. For example, in some implementations, an electronic watch, a smartphone or a tablet can be attached to the head-mountable enclosure. In various implementations, the head-mountable enclosure is shaped to form a receptacle for receiving another device that includes a display (e.g., an electronic watch, a smartphone or a tablet). For example, in some implementations, a device with a display slides/snaps into or otherwise attaches to the head-mountable enclosure. In some implementations, the display of the device attached to the head-mountable enclosure presents (e.g., displays) the XR environment. In various implementations, examples of the electronic device 20 include smartphones, tablets, media players, laptops, etc.

Figure 2:
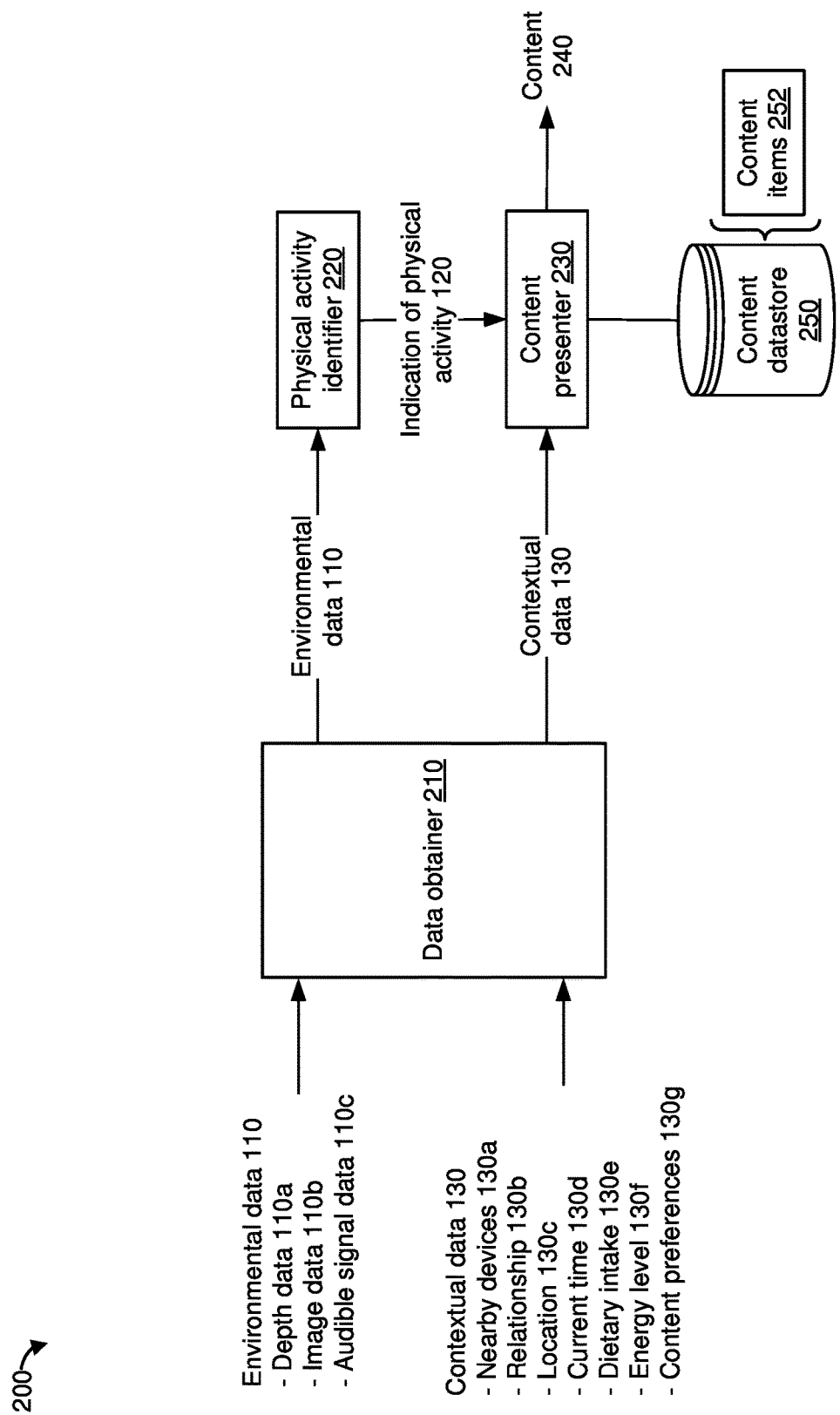
FIG. 2 is a block diagram of a system in accordance with some implementations.

FIG. 2 is a block diagram of a system 200 in accordance with some implementations. In some implementations, the system 200 resides at (e.g., is implemented by) the electronic device 20 shown in FIGS. 1A-1F. In some implementations, the electronic device 20 (shown in FIGS. 1A-1F) includes the system 200. In various implementations, the system 200 includes a data obtainer 210, a physical activity identifier 220, a content presenter 230 and a content datastore 250.

In various implementations, the data obtainer 210 obtains the environmental data 110 and the contextual data 130. In some implementations, the environmental data 110 includes depth data 110a that the data obtainer 210 receives from a depth sensor (e.g., a depth camera). In some implementations, the environmental data 110 includes image data 110b (e.g., a set of one or more images) that the data obtainer 210 receives from an image sensor (e.g., a camera). In some implementations, the depth data 110a and/or the image data 110b indicate a movement of the user 30 shown in FIGS. 1A-1F. For example, the depth data 110a and/or the image data 110b indicate a body pose of the user 30. In some implementations, the body pose includes respective positions and/or respective orientations of various body portions of the user 30. For example, the body pose is defined by respective position values and/or respective orientation values for a head, shoulder joints, elbow joints, hip joint, knee joints, and ankle joints of the user 30.

In some implementations, the environmental data 110 includes audible signal data 110c (e.g., electronic signal data) that the data obtainer 210 receives from an audio sensor (e.g., a microphone). In some implementations, the audio sensor receives an audible signal that is converted into the audible signal data 110c. In some implementations, the audible signal data 110c represents speech being spoken by the user 30. In some implementations, the audible signal data 110c represents sounds in the physical environment. In various implementations, the audible signal data 110c indicates the physical activity of the user 30.

As described in relation to FIG. 1C, in some implementations, the data obtainer 210 obtains contextual data 130 that includes information regarding nearby devices 130a. For example, in some implementations, the contextual data 130 indicates types of the nearby devices 130a (e.g., whether there is a speaker or a television within a threshold distance of the user 30). As described in relation to FIG. 1D, in some implementations, the data obtainer 210 obtains contextual data 130 that indicates the relationship 130b between the user 30 and another person in the physical environment. As described in relation to FIG. 1E, in some implementations, the data obtainer 210 obtains contextual data 130 that indicates the location 130c of the electronic device 20. As described in relation to FIG. 1F, in some implementations, the data obtainer 210 obtains contextual data 130 that indicates the current time 130d.

In some implementations, the data obtainer 210 obtains contextual data 130 that includes a dietary intake 130e of the user 30. In some implementations, the dietary intake 130e indicates a number of calories that the user 30 has consumed. In some implementations, the data obtainer 210 obtains contextual data 130 that indicates an energy level 130f of the user 30. In some implementations, the energy level 130f indicates whether the user 30 is tired, lethargic, or energetic. In some implementations, the data obtainer 210 obtains contextual data 130 that indicates content preferences 130g of the user 30. In some implementations, the content preferences 130g indicate a presentation mode that the user 30 prefers. For example, the content preferences 130g indicate whether the user 30 prefers an audio presentation mode, a video presentation mode or an AR presentation mode.

In various implementations, the physical activity identifier 220 obtains the environmental data 110 from the data obtainer 210, and the physical activity identifier 220 identifies a physical activity that the user 30 is engaged in based on the environmental data 110. The physical activity identifier 220 generates the indication 120 of the physical activity after identifying the physical activity that the user 30 is performing.

In some implementations, the physical activity identifier 220 identifies the physical activity of the user 30 based on the depth data 110a or the image data 110b. In some implementations, the physical activity identifier 220 determines a body pose of the user 30 based on the depth data 110a or the image data 110b. In some implementations, the physical activity identifier 220 compares the body pose of the user 30 with body poses corresponding to a set of known activities. In some such implementations, the physical activity identifier 220 selects a particular activity from the set of known activities when the body pose of the user is within a similarity threshold of the body pose corresponding to that particular activity (e.g., when the body pose of the user matches the body pose of that particular activity).

In some implementations, the physical activity identifier 220 identifies the physical activity of the user 30 based on the audible signal data 110c. In some implementations, the physical activity identifier 220 compares the audible signal data 110c with audio signatures corresponding to a set of known activities. In some such implementations, the physical activity identifier 220 selects a particular activity from the set of known activities when the audible signal data 110c is within a similarity threshold of an audio signature that corresponds to that particular activity (e.g., when the audible signal data 110c matches the audio signature of that particular activity).

In some implementations, the physical activity identifier 220 identifies the physical activity of the user 30 based on motion data from a motion sensor (e.g., an inertial measuring unit (IMU) in the electronic device 20 or another device that the user 30 is holding or wearing). In some implementations, the physical activity identifier 220 compares the motion data with motion signatures (e.g., motion patterns) corresponding to a set of known activities. In some such implementations, the physical activity identifier 220 selects a particular activity from the set of known activities when the motion data is within a similarity threshold of a motion signature that corresponds to that particular activity (e.g., when the motion data matches the motion signature of that particular activity).

In various implementations, the physical activity identifier 220 identifies the physical activity of the user 30 based on a combination of the depth data 110a, the image data 110b, the audible signal data 110d and the motion data. In some implementations, the physical activity identifier 220 receives a user input that specifies the physical activity of the user 30.

In various implementations, the content presenter 230 presents content 240 based on the indication 120 of the physical activity and the contextual data 130. In some implementations, the content presenter 230 selects the content 240 from the content datastore 250 that stores various media content items 252 ("content items 252", hereinafter for the sake of brevity).

In some implementations, the content presenter 230 selects a content item 252 that is relevant to the physical activity. For example, if the user 30 is performing a dance move, the content presenter 230 identifies music items that match the dance move. As an example, if the dance move is popping and locking, then content presenter 230 selects a music item (e.g., a song or a music video) from the hip hop genre. As another example, if the dance move is an arabesque where the body of the user 30 is supported on one leg with the other leg extended directly behind the body with a straight knee, the content presenter 230 selects a music item from the classical music genre.

In some implementations, the content presenter 230 selects a content item 252 that is relevant to the physical activity and a context indicated by the contextual data 130. In some implementations, the content presenter 230 selects a content item 252 that can be presented on one of the nearby devices 130a. For example, in some implementations, if there is a speaker (e.g., the speaker 140 shown in FIG. 1C) near the user 30, the content presenter 230 selects an audio content item related to the physical activity from the content datastore 250. In another example, if there is a television near the user 30, the content presenter 230 selects a video content item related to the physical activity from the content datastore 250.

In some implementations, the content presenter 230 selects a content item 252 that is relevant to the physical activity and is suitable for the relationship 130b between the user 30 and another person in the physical environment. For example, in some implementations, if the user 30 is dancing with his/her spouse, the content presenter 230 selects, from the content datastore 250, a music item from a romantic music genre. In another example, if the user 30 is dancing with his/her child, the content presenter 230 selects, from the content datastore 250, a music video from a kid's music genre.

In some implementations, the content presenter 230 selects a content item 252 that is relevant to the physical activity and is appropriate for the location 130c of the electronic device 20. For example, in some implementations, if the user 30 is dancing in a public place (e.g., a park), the content presenter 230 plays a public dance playlist. In another example, if the user 30 is dancing in a private place (e.g., at his/her home), the content presenter 230 plays a private dance playlist.

In some implementations, the content presenter 230 selects a content item 252 that is relevant to the physical activity and is suitable for the current time 130d. For example, in some implementations, if the user 30 is sitting and eating in the morning, the content presenter 230 plays morning news (e.g., a news channel or a news radio station). In another example, if the user 30 is sitting and eating in the evening, the content presenter 230 plays an episode from a sitcom.

In some implementations, the content presenter 230 selects a content item 252 that is relevant to the physical activity and is based on a dietary intake 130e of the user 30. For example, in some implementations, if the user 30 is dancing and the dietary intake 130e indicates that the user 30 has not eaten food for a few hours (e.g., within a threshold amount of time), the content presenter 230 selects songs with a fast beat that encourages the user 30 to perform relatively fast dance moves. In another example, if the user 30 is dancing and the dietary intake 130e indicates that the user 30 has just finished a big meal, the content presenter 230 selects songs with a slow beat that invites the user 30 to perform relatively slower dance moves.

In some implementations, the content presenter 230 selects a content item 252 that is relevant to the physical activity and is based on an energy level 130f of the user 30. For example, in some implementations, if the user 30 is dancing and the energy level 130f of the user 30 is relatively high (e.g., above a threshold), the content presenter 230 selects music with a fast beat that encourages the user 30 to perform relatively fast dance moves. In another example, if the user 30 is dancing and the energy level 130f of the user 30 is relatively low (e.g., below the threshold), the content presenter 230 selects a music item with a slow beat that invites the user 30 to perform relatively slower dance moves or to relax and listen to the music.

In some implementations, the content presenter 230 selects a content item 252 that is relevant to the physical activity and matches the content preferences 130g of the user 30. For example, in some implementations, if the user 30 is dancing and the content preferences 130g indicate that the user 30 likes to watch music videos, the content presenter 230 selects a music video that matches the dance moves of the user 30 from the content datastore 250. In another example, if the user 30 is dancing and the content preferences 130g indicate that the user 30 likes to listen to songs, the content presenter 230 selects a song that matches the dance moves of the user 30 from the content datastore 250. In another example, if the user 30 is dancing and the content preferences 130g indicate that the user 30 likes to view AR content, the content presenter 230 selects an AR content item that matches the dance moves of the user 30 from the content datastore 250 (e.g., the content presenter 230 selects a virtual character that dances along with the user 30).

In various implementations, the content presenter 230 generates the content 240 by combining some of the content items 252. For example, in some implementations, the content presenter 230 identifies a subset of the content items 252 that are relevant based on the physical activity and the contextual data 130. In such implementations, the content presenter 230 combines some of the content items 252 in the subset in order to generate the content 240.

Figure 3:
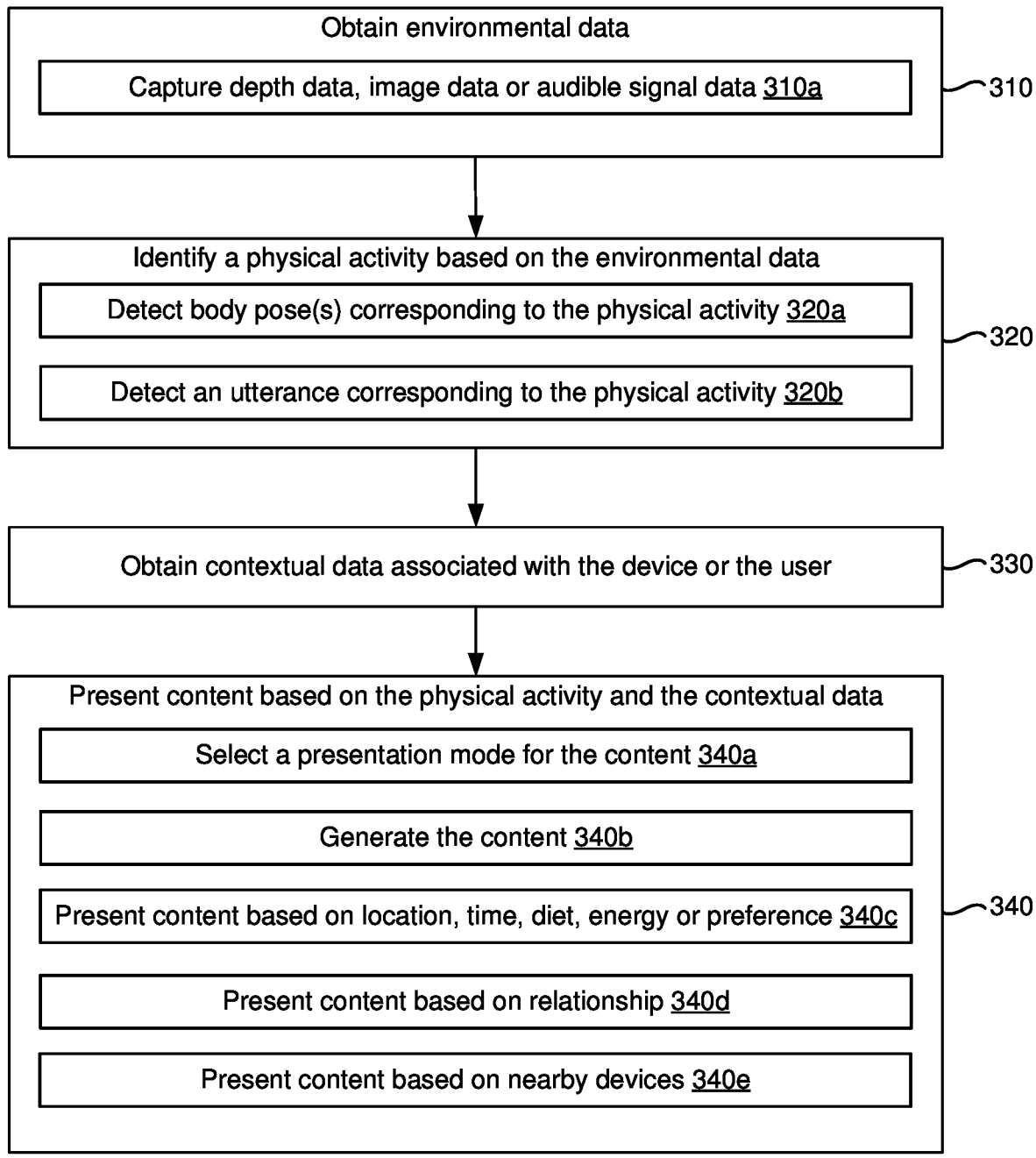
FIG. 3 is a flowchart representation of a method of presenting content based on activity in accordance with some implementations.

FIG. 3 is a flowchart representation of a method 300 of presenting content based on activity. In various implementations, the method 300 is performed by a device with a sensor, a non-transitory memory and one or more processors coupled with the sensor and the non-transitory memory (e.g., the electronic device 20 shown in FIGS. 1A-1F, and/or the system 200 shown in FIG. 2). In some implementations, the method 300 is performed by processing logic, including hardware, firmware, software, or a combination thereof. In some implementations, the method 300 is performed by a processor executing code stored in a non-transitory computer-readable medium (e.g., a memory).

As represented by block 310, in some implementations, the method 300 includes obtaining environmental data via the sensor. As represented by block 310a, in some implementations, the sensor includes a depth sensor (e.g., a depth camera), and obtaining the environmental data includes capturing depth data via the depth sensor. For example, as shown in FIG. 2, the data obtainer 210 obtains the depth data 110a.

In some implementations, the sensor includes an image sensor (e.g., a camera), and obtaining the environmental data includes capturing image data (e.g., a set of one or more images) via the image sensor. For example, as shown in FIG. 2, the data obtainer 210 obtains the image data 110b.

In some implementations, the sensor includes an audio sensor (e.g., a microphone), and obtaining the environmental data includes receiving an audible signal at the audio sensor and converting the audible signal into audible signal data (e.g., the audible signal data 110c shown in FIG. 1C). In some implementations, the sensor includes a motion sensor (e.g., an IMU), and obtaining the environmental data includes capturing motion data (e.g., IMU data) via the motion sensor.

As represented by block 320, in some implementations, the method 300 includes identifying a physical activity of a user of the device based on the environmental data. For example, as shown in FIGS. 1A-2, the electronic device 20 (e.g., the physical activity identifier 220) provides the indication 120 of the physical activity based on the environmental data 110.

As represented by block 320a, in some implementations, identifying the physical activity includes detecting, based on the environmental data, a sequence of body poses that correspond to the physical activity. For example, detecting a quarter-turn in a torso of a person indicating that the person is performing a twirl. In some implementations, the method 300 includes detecting the sequence of body poses of the user based on depth data and/or image data captured by the device. In some implementations, the method 300 includes comparing the sequence of body poses with body poses associated with a set of known activities, and determining that the user of the device is performing a particular activity from the set of known activities when the sequence of body poses of the user match the body poses associated with that particular activity.

As represented by block 320b, in some implementations, the sensor includes an audio sensor (e.g., a microphone) and the environmental data includes audible signal data captured by the audio sensor. In some implementations, identifying the physical activity includes detecting, based on the audible signal data, an utterance that corresponds to the physical activity. For example, detecting an utterance that corresponds to an imitation of a lion's roar tends to indicate that the user is pretending to be a lion. In some implementations, the method 300 includes comparing the audible signal data with audio signatures (e.g., sounds) associated with known activities, and determining that the user of the device is performing a particular activity from the set of known activities when the audible signal data (e.g., the utterance) matches the audio signature associated with that particular activity.

In some implementations, the sensor includes a motion sensor (e.g., an IMU) and the environmental data includes motion data captured by the motion sensor. In some implementations, identifying the physical activity includes detecting, based on the motion data, a body movement that corresponds to the physical activity. For example, detecting a movement that corresponds to performing a squat. In some implementations, the method 300 includes comparing the motion data with motion patterns associated with known activities, and determining that the user of the device is performing a particular activity from the set of known activities when the motion data (e.g., the user's movement) matches the motion pattern associated with that particular activity.

As represented by block 330, in some implementations, the method 300 includes obtaining contextual data associated with the device or the user of the device. For example, as shown in FIGS. 1A-1F, the electronic device 20 obtains the contextual data 130. In some implementations, obtaining the contextual data includes obtaining information regarding devices that are within a threshold distance of the device (e.g., the information regarding nearby devices 130a shown in FIGS. 1C and 2). In some implementations, obtaining the contextual data includes obtaining information indicating a relationship between the user of the device and another person location within a threshold distance of the user (e.g., the information regarding the relationship 130b shown in FIGS. 1D and 2). In some implementations, obtaining the contextual data includes determining a type of relationship between the user and another person located in the physical environment (e.g., determining whether the type of relationship is a familial relationship, a collegial relationship, a parent-child relationship or a close friendship). In some implementations, the method 300 includes utilizing information stored in a contacts application to determine the type of relationship between the user and the other person in the physical environment (e.g., identifying a contact entry with a profile photo that matches a facial image captured by a camera of the device).

In some implementations, obtaining the contextual data includes obtaining a location of the device (e.g., the location 130c shown in FIGS. 1E and 2). In some implementations, obtaining the location of the device includes determining a type of location of the device (e.g., determining whether the location of the device corresponds to a private location where persons unknown to the user are not present or a public location where persons unknown to the user are present).

In some implementations, obtaining the contextual data includes obtaining information regarding a dietary intake of the user (e.g., the dietary intake 130e shown in FIG. 2, for example, from a food-tracking application). In some implementations, obtaining the contextual data includes obtaining information regarding an energy level of the user (e.g., the energy level 130f shown in FIG. 2). In some implementations, obtaining the contextual data includes obtaining information regarding content preferences 130g of the user (e.g., the content preferences 130g shown in FIG. 2).

In various implementations, obtaining the contextual data includes detecting the contextual data via a sensor (e.g., detecting the location of the device via a global position system (GPS) sensor). In some implementations, obtaining the contextual data includes retrieving the information from an application via an application programming interface (API) (e.g., retrieving the dietary intake and energy level from a health application or a food-tracking application). In some implementations, obtaining the contextual data includes retrieving the information from settings of the device (e.g., retrieving the content preferences from the settings of the device). In some implementations, obtaining the contextual data includes determining the contextual data based on a historical usage pattern of the device (e.g., determining the content preferences based on the types of content items that the user has requested the device to present). In some implementations, obtaining the contextual data includes receiving information from other devices (e.g., receiving beacons from other devices in order to determine types of other devices that are within a threshold distance of the device, for example, determining nearby devices).

As represented by block 340, in various implementations, the method 300 includes presenting content based on the physical activity of the user and the contextual data associated with the device or the user of the device. For example, as shown in FIG. 1A, the electronic device 20 presents the content 100 based on the indication 120 of the physical activity of the user 30 and the contextual data 130. In various implementations, presenting content based on the physical activity and the contextual data enhances a user experience of the device by ensuring that the content is relevant to the physical activity and appropriate based on a context indicated by the contextual data. In some implementations, presenting content based on the physical activity and the contextual data tends to increase a likelihood of the user engaging with the content thereby preventing unnecessary battery drainage that results from presenting content that the user does not engage with.

As represented by block 340a, in some implementations, presenting the content includes selecting a presentation mode for the content from a plurality of presentation modes based on the physical activity or the contextual data. In some implementations, the method 300 includes selecting a presentation mode in which the user is more likely to engage with the content, and forgoing selection of a presentation mode in which the user is less likely to engage with the content. In some implementations, the method 300 includes determining a likelihood of the user engaging with the content in each of the presentation modes based on the physical activity or the contextual data, and selecting the presentation mode that is associated with the greatest likelihood of user engagement.

In some implementations, presenting the content includes selecting an audio presentation mode for the content based on the physical activity or the contextual data, and playing an audio representation of the content. For example, as shown in FIG. 1B, the electronic device 20 plays the audio 100a. As an example, if the physical activity is a scavenger hunt, the electronic device outputs an audible signal that corresponds to a verbal instruction for the user to pick up a virtual gold coin from behind a physical couch in the physical environment. In some implementations, the method 300 includes selecting the audio presentation mode when the physical activity or the contextual data indicate that the user is not in a position to view content (e.g., because the physical activity requires the user's visual attention).

In some implementations, presenting the content includes selecting a visual presentation mode for the content when the contextual data indicates that there is a display screen within a threshold distance of the device, and displaying a video representation of the content on the display screen. For example, in some implementations, the method 300 includes playing a video on a nearby TV, for example, instead of or in addition to playing the video on a display of the device. In some implementations, the method 300 includes selecting the video presentation mode when the physical activity or the contextual data indicate that the user is available to view content (e.g., because the physical activity does not require the user's visual attention).

In some implementations, presenting the content includes selecting an augmented reality (AR) presentation mode for the content based on a semantic analysis of the physical activity, and displaying an AR representation of the content. As an example, if the user is imitating breathing out dragon fire, the device displays virtual fire coming out of the user's mouth. As another example, the device displays a virtual character that performs the physical activity with the user. For example, if the user is practicing dancing, the virtual character helps the user in learning a new dance move.

As represented by block 340*b*, in some implementations, the method 300 includes generating the content based on a semantic analysis of the physical activity of the user. As an example, if the user is playing truth or dare, the device generates dares for the user. Content generated based on a semantic analysis of the physical activity tends to be more relevant than other content.

In some implementations, presenting the content includes generating a narrative based on a semantic analysis of the physical activity of the user and presenting the narrative. For example, if the user is telling a story and the user is unable to complete a portion of the story, the device generates the portion of the story that the user is unable to complete. In some implementations, presenting the narrative includes outputting an audible signal that corresponds to the narrative.

In some implementations, presenting the content includes selecting a story template based on the physical activity and presenting content that corresponds to the story template. As an example, if the user is engaged in a scavenger hunt, the device adds more items to a list of items as the user finds items on the list. Content that fits the story template tends to be more related to the physical activity than other content that does not fit the story template.

In some implementations, presenting the content includes selecting a media content item from a set of existing media content items. For example, as shown in FIG. 2, in some implementations, the content presenter 230 selects one or more of the content items 252 from the content datastore 250. In some implementations, presenting the content includes synthesizing the content based on a set of existing media content items. In some implementations, the method 300 includes generating the content by combining a subset of a set of existing media content items. As an example, referring to FIG. 2, in some implementations, the content presenter 230 generates the content 240 by combining a subset of the content items 252 in the content datastore 250.

In some implementations, the method 300 includes generating the content by combining a set of existing sound effects.

As represented by block 340*c*, in some implementations, the contextual data indicates a location of the device. In such implementations, presenting the content includes presenting a first media content item when the location of the device corresponds to a first type of location (e.g., a public location), and presenting a second media content item that is different from the first media content item when the location of the device corresponds to a second type of location that is different from the first type of location (e.g., a private location). For example, as shown in FIG. 1E, the electronic device 20 displays the content 100*c* based on the location 130*c*.

In some implementations, the contextual data indicates a current time. In such implementations, presenting the content includes presenting a first media content item when the current time is within a first time range (e.g., when it is morning), and presenting a second media content item that is different from the first media content item when the current time is within a second time range that is different from the first time range (e.g., when it is evening). For example, as shown in FIG. 1F, the electronic device 20 displays the content 100*d* based on the current time 130*d*.

In some implementations, the contextual data indicates a dietary intake of the user. In such implementations, presenting the content includes presenting a first media content item when the dietary intake of the person corresponds to a first amount of food or a first type of food (e.g., when the user had a big/heavy meal), and presenting a second media content item that is different from the first media content item when the dietary intake of the person corresponds to a second amount of food that is different from the first amount of food or a second type of food that is different from the first type of food (e.g., when the user had a small/light meal). For example, as shown in FIG. 2, the system 200 displays the content 240 based on the dietary intake 130*e*.

In some implementations, the contextual data indicates an energy level of the user. In such implementations, presenting the content includes presenting a first media content item when the energy level of the user satisfies a threshold energy level (e.g., when the energy level of the user exceeds the threshold energy level, for example, when the user has a relatively high amount of energy), and presenting a second media content item that is different from the first media content item when the energy level of the user breaches the threshold energy level (e.g., when the energy level of the user is below the threshold energy level, for example, when the user has a relatively low amount of energy). For example, as shown in FIG. 2, the system 200 presents the content 240 based on the energy level 130*f*.

In some implementations, the contextual data indicates a content preference of the user. In such implementations, presenting the content includes presenting a first media content item when the content preference of the person corresponds to a first type of content (e.g., playing a musical sound from a heavy metal music genre, if the user likes heavy metal music), and presenting a second media content item that is different from the first media content item when the content preference of the person corresponds to a second type of content that is different from the first type of content (e.g., playing a musical sound from a classical music genre, if the user likes classical music). For example, as shown in FIG. 2, the system 200 presents the content 240 based on the content preferences 130*g*.

As represented by block 340*d*, in some implementations, the contextual data indicates a relationship of the user with a person that is within a threshold distance of the user (e.g., in the same physical environment as the user). In such implementations, presenting the content includes presenting a first media content item when the relationship corresponds to a first type of relationship (e.g., a familial relationship), and presenting a second media content item that is different from the first media content item when the relationship corresponds to a second type of relationship that is different from the first type of relationship (e.g., a collegial relationship). For example, as shown in FIG. 1D, the electronic device 20 presents the content 100*b* based on the relationship 130*b* between the user 30 and the person 150.

As represented by block 340*e*, in some implementations, the contextual data indicates a type of another device that is within a threshold distance of the device (e.g., in the same physical environment as the user). In such implementations, presenting the content includes presenting the content via a first presentation mode when the type of the other device corresponds to a first type of device (e.g., presenting the content via an audio presentation mode when the type of the other device is a speaker), and presenting the content via a second presentation mode that is different from the first presentation mode when the type of the other device corresponds to a second type of device that is different from the first type of device (e.g., presenting the content via a video presentation mode when the type of the other device is a display, for example, a television). For example, as shown in FIG. 1C, the electronic device 20 causes the speaker 140 to play the audio 100*a* when the contextual data 130 includes information regarding nearby devices 130*a* indicating that the speaker 140 is within a threshold distance of the electronic device 20.

In some implementations, the method 300 includes detecting that the user is holding an object, and generating the content based on movement of the object. As an example, the device detects that the user is holding a broomstick, and the device outputs a swishing sound as the user hurls the broomstick around in order to make the movement of the broomstick sound similar to the movement of a sword being moved around.

Figure 4:
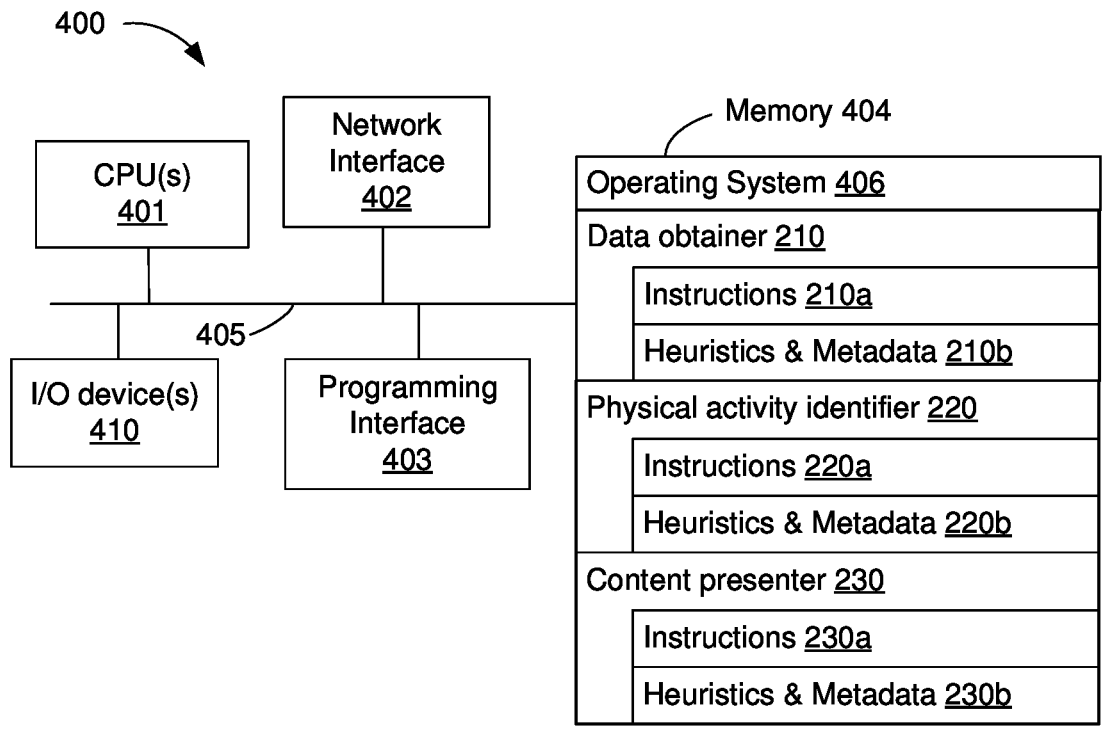
FIG. 4 is a block diagram of a device that presents content based on activity in accordance with some implementations.

FIG. 4 is a block diagram of a device 400 that presents content based on activity in accordance with some implementations. In some implementations, the device 400 implements the electronic device 20 shown in FIGS. 1A-1F, and/or the system 200 shown in FIG. 2. While certain specific features are illustrated, those of ordinary skill in the art will appreciate from the present disclosure that various other features have not been illustrated for the sake of brevity, and so as not to obscure more pertinent aspects of the implementations disclosed herein. To that end, as a non-limiting example, in some implementations the device 400 includes one or more processing units (CPUs) 401, a network interface 402, a programming interface 403, a memory 404, one or more input/output (I/O) devices 410, and one or more communication buses 405 for interconnecting these and various other components.

In some implementations, the network interface 402 is provided to, among other uses, establish and maintain a metadata tunnel between a cloud hosted network management system and at least one private network including one or more compliant devices. In some implementations, the one or more communication buses 405 include circuitry that interconnects and controls communications between system components. The memory 404 includes high-speed random access memory, such as DRAM, SRAM, DDR RAM or other random access solid state memory devices, and may include non-volatile memory, such as one or more magnetic disk storage devices, optical disk storage devices, flash memory devices, or other non-volatile solid state storage devices. The memory 404 optionally includes one or more storage devices remotely located from the one or more CPUs 401. The memory 404 comprises a non-transitory computer readable storage medium.

In some implementations, the memory 404 or the non-transitory computer readable storage medium of the memory 404 stores the following programs, modules and data structures, or a subset thereof including an optional operating system 406, the data obtainer 210, the physical activity identifier 220 and the content presenter 230. In various implementations, the device 400 performs the method 300 shown in FIG. 3.

In some implementations, the data obtainer 210 obtains environmental data and contextual data. In some implementations, the data obtainer 210 performs the operation(s) represented by blocks 310 and 330 in FIG. 3. To that end, the data obtainer 210 includes instructions 210*a*, and heuristics and metadata 210*b*.

In some implementations, the physical activity identifier 220 identifies a physical activity of the user based on the environmental data. In some implementations, the physical activity identifier 220 performs the operation(s) represented by block 320 in FIG. 3. To that end, the physical activity identifier 220 includes instructions 220*a*, and heuristics and metadata 220*b*.

In some implementations, the content presenter 230 presents content based on the physical activity and the contextual data. In some implementations, the content presenter 230 performs the operation(s) represented by block 340 in FIG. 3. To that end, the content presenter 230 includes instructions 230*a*, and heuristics and metadata 230*b*.

In various implementations, the one or more I/O devices 410 include an environmental sensor for capturing environmental data (e.g., the environmental data 110 shown in FIGS. 1A-2). For example, in some implementations, the one or more I/O devices 410 include an audio sensor (e.g., a microphone) for receiving an audible signal (e.g., for capturing the audible signal data 110*c* shown in FIG. 2). In some implementations, the one or more I/O devices 410 include an image sensor (e.g., a camera) to capture image data (e.g., for capturing the image data 110*b* shown in FIG. 2). In some implementations, the one or more I/O devices 410 include a depth sensor (e.g., a depth camera) to capture the depth data (e.g., for capturing the depth data 110*a* shown in FIG. 2). In some implementations, the one or more I/O devices 410 include a display for displaying content (e.g., the content 100 shown in FIG. 1A, the content 100*b* shown in FIG. 1D, the content 100*c* shown in FIG. 1E, the content 100*d* shown in FIG. 1F, of the content 240 shown in FIG. 2). In some implementations, the one or more I/O devices 410 include a speaker for outputting an audible signal (e.g., the audio 100*a* shown in FIG. 1B).

In various implementations, the one or more I/O devices 410 include a video pass-through display which displays at least a portion of a physical environment surrounding the device 400 as an image captured by a scene camera. In various implementations, the one or more I/O devices 410 include an optical see-through display which is at least partially transparent and passes light emitted by or reflected off the physical environment.

While various aspects of implementations within the scope of the appended claims are described above, it should be apparent that the various features of implementations described above may be embodied in a wide variety of forms and that any specific structure and/or function described above is merely illustrative. Based on the present disclosure one skilled in the art should appreciate that an aspect described herein may be implemented independently of any other aspects and that two or more of these aspects may be combined in various ways. For example, an apparatus may be implemented and/or a method may be practiced using any number of the aspects set forth herein. In addition, such an apparatus may be implemented and/or such a method may be practiced using other structure and/or functionality in addition to or other than one or more of the aspects set forth herein.

It will also be understood that, although the terms "first", "second", etc. may be used herein to describe various elements, these elements should not be limited by these terms. These terms are only used to distinguish one element from another. For example, a first node could be termed a second node, and, similarly, a second node could be termed a first node, which changing the meaning of the description, so long as all occurrences of the "first node" are renamed consistently and all occurrences of the "second node" are renamed consistently. The first node and the second node are both nodes, but they are not the same node.

The terminology used herein is for the purpose of describing particular implementations only and is not intended to be limiting of the claims. As used in the description of the implementations and the appended claims, the singular forms "a", "an", and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising", when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in accordance with a determination" or "in response to detecting", that a stated condition precedent is true, depending on the context. Similarly, the phrase "if it is determined [that a stated condition precedent is true]" or "if [a stated condition precedent is true]" or "when [a stated condition precedent is true]" may be construed to mean "upon determining" or "in response to determining" or "in accordance with a determination" or "upon detecting" or "in response to detecting" that the stated condition precedent is true, depending on the context.

What is claimed is:

1. A method comprising:
    at a first device including a sensor, a non-transitory memory and one or more processors coupled with the sensor and the non-transitory memory:
        obtaining environmental data via the sensor;
        identifying a physical activity of a user of the first device based on the environmental data;
        in response to a plurality of content items being relevant to the physical activity of the user, obtaining contextual data indicating a type of a second device that is within a threshold distance of the first device, wherein the second device is different from the first device; and
        presenting a subset of the plurality of content items based on the physical activity of the user and the type of the second device that is within the threshold distance of the first device.

2. The method of claim 1, wherein the presenting comprises selecting a presentation mode from a plurality of presentation modes based on the physical activity and the type of the second device.

3. The method of claim 1, wherein the presenting comprises:
    selecting an audio presentation mode based on the physical activity and the second device being a speaker; and
    playing, via the speaker, an audio representation of the subset of the plurality of content items.

4. The method of claim 1, wherein the presenting comprises:
    selecting a visual presentation mode when the contextual data indicates that the second device includes a display screen; and
    displaying a video representation of the subset of the plurality of content items on the display screen.

5. The method of claim 1, wherein the presenting comprises:
    selecting an augmented reality (AR) presentation mode based on a semantic analysis of the physical activity; and
    displaying an AR representation of the subset of the plurality of content items.

6. The method of claim 1, further comprising:
    detecting that the user is holding an object; and
    selecting the subset of the plurality of content items based on movement of the object.

7. The method of claim 1, wherein the presenting comprises generating a narrative based on a semantic analysis of the physical activity of the user and presenting the subset of the plurality of content items in response to the subset of the plurality of content items corresponding to the narrative.

8. The method of claim 1, wherein the presenting comprises selecting a story template based on the physical activity and presenting the subset of the plurality of content items in response to the subset of the plurality of content items corresponding to the story template.

9. The method of claim 1, wherein the contextual data further indicates a location of the first device; and
    wherein the presenting comprises:
        presenting a first media content item from the plurality of content items when the location of the first device corresponds to a first type of location; and
        presenting a second media content item from the plurality of content items that is different from the first media content item when the location of the first device corresponds to a second type of location that is different from the first type of location.

10. The method of claim 1, wherein the contextual data further indicates a current time; and
    wherein the presenting comprises:
        presenting a first media content item from the plurality of content items when the current time is within a first time range; and
        presenting a second media content item from the plurality of content items that is different from the first media content item when the current time is within a second time range that is different from the first time range.

11. The method of claim 1, wherein the contextual data further indicates a dietary intake of the user; and
wherein the presenting comprises:
presenting a first media content item from the plurality of content items when the dietary intake of the person corresponds to a first amount of food or a first type of food; and
presenting a second media content item from the plurality of content items that is different from the first media content item when the dietary intake of the person corresponds to a second amount of food that is different from the first amount of food or a second type of food that is different from the first type of food.

12. The method of claim 1, wherein the contextual data further indicates an energy level of the user; and
wherein the presenting comprises:
presenting a first media content item from the plurality of content items when the energy level of the user satisfies a threshold energy level; and
presenting a second media content item from the plurality of content items that is different from the first media content item when the energy level of the user breaches the threshold energy level.

13. The method of claim 1, wherein the contextual data further indicates a content preference of the user; and
wherein the presenting comprises:
presenting a first media content item from the plurality of content items when the content preference of the person corresponds to a first type of content; and
presenting a second media content item from the plurality of content items that is different from the first media content item when the content preference of the person corresponds to a second type of content that is different from the first type of content.

14. The method of claim 1, wherein the contextual data further indicates a relationship of the user with a person that is within a threshold distance of the user; and
wherein the presenting comprises:
presenting a first media content item from the plurality of content items when the relationship corresponds to a first type of relationship; and
presenting a second media content item from the plurality of content items that is different from the first media content item when the relationship corresponds to a second type of relationship that is different from the first type of relationship.

15. The method of claim 1, wherein the presenting comprises:
presenting via a first presentation mode when the type of the second device corresponds to a first type of device; and
presenting via a second presentation mode that is different from the first presentation mode when the type of the second device corresponds to a second type of device that is different from the first type of device.

16. A non-transitory memory storing one or more programs, which, when executed by one or more processors of a first device, cause the first device to:
obtain environmental data via a sensor;
identify a physical activity of a user of the first device based on the environmental data;
in response to a plurality of content items being relevant to the physical activity of the user, obtain contextual data indicating a type of a second device that is within a threshold distance of the first device, wherein the second device is different from the first device; and
present a subset of the plurality of content items based on the physical activity of the user and the type of the second device that is within the threshold distance of the first device.

17. The non-transitory memory of claim 16, wherein presenting the subset of the plurality of content items comprises:
selecting an audio presentation mode based on the physical activity and the second device being a speaker; and
playing, via the speaker, an audio representation of the subset of the plurality of content items.

18. The non-transitory memory of claim 16, wherein the one or more programs further cause the first device to:
detect that the user is holding an object; and
select the subset of the plurality of content items based on movement of the object.

19. The non-transitory memory of claim 16, wherein the contextual data further indicates a location of the first device; and
wherein presenting the subset of the plurality of content items comprises:
presenting a first media content item from the plurality of content items when the location of the first device corresponds to a first type of location; and
presenting a second media content item from the plurality of content items that is different from the first media content item when the location of the first device corresponds to a second type of location that is different from the first type of location.

20. A first device comprising:
a sensor;
one or more processors;
a non-transitory memory;
one or more displays; and
one or more programs stored in the non-transitory memory, which, when executed by the one or more processors, cause the first device to:
obtain environmental data via the sensor;
identify a physical activity of a user of the first device based on the environmental data;
in response to a plurality of content items being relevant to the physical activity of the user, obtain contextual data indicating a type of a second device that is within a threshold distance of the first device, wherein the second device is different from the first device; and
present a subset of the plurality of content items based on the physical activity of the user and the type of the second device that is within the threshold distance of the first device.

21. The first device of claim 20, wherein presenting the subset of the plurality of content items comprises:
selecting an augmented reality (AR) presentation mode based on a semantic analysis of the physical activity; and
displaying an AR representation of the subset of the plurality of content items.

22. The first device of claim 20, wherein presenting the subset of the plurality of content items comprises selecting a story template based on the physical activity and presenting the subset of the plurality of content items in response to the subset of the plurality of content items corresponding to the story template.

23. The first device of claim 20, wherein the contextual data further indicates a current time; and
wherein presenting the subset of the plurality of content items comprises:

presenting a first media content item from the plurality of content items when the current time is within a first time range; and presenting a second media content item from the plurality of content items that is different from the first media content item when the current time is within a second time range that is different from the first time range.

* * * * *

UNITED STATES PATENT AND TRADEMARK OFFICE
CERTIFICATE OF CORRECTION

| | | |
|---|---|---|
| PATENT NO. | : 11,726,551 B1 | Page 1 of 1 |
| APPLICATION NO. | : 17/381957 | |
| DATED | : August 15, 2023 | |
| INVENTOR(S) | : Ian M. Richter | |

It is certified that error appears in the above-identified patent and that said Letters Patent is hereby corrected as shown below:

In the Claims

Claim 1, Line 64 currently reads:
"contextual indicating a type of a second device"
And should instead read:
"contextual data indicating a type of a second device".

Signed and Sealed this
Twenty-fourth Day of October, 2023

Katherine Kelly Vidal
*Director of the United States Patent and Trademark Office*